United States Patent [19]

Langford et al.

[11] Patent Number: 5,753,195
[45] Date of Patent: May 19, 1998

[54] CLEANING AND STERILIZING MECHANISM

[75] Inventors: Terrence R. Langford, Tucson, Ariz.; David L. Davis, Indianola, Wash.

[73] Assignee: Kew Import/Export Inc., Tucson, Ariz.

[21] Appl. No.: 582,849

[22] Filed: Jan. 2, 1996

[51] Int. Cl.[6] .................................................. A61L 2/00
[52] U.S. Cl. .................. 422/292; 134/169 R; 134/170; 422/294; 422/295; 422/297; 422/300
[58] Field of Search ..................... 422/292, 294, 422/295, 297, 300; 134/170, 169 R

[56] References Cited

U.S. PATENT DOCUMENTS

| | | | |
|---|---|---|---|
| 2,499,162 | 2/1950 | Rand . | |
| 3,910,761 | 10/1975 | Hopkins . | |
| 4,010,786 | 3/1977 | Aguettant et al. . | |
| 4,194,622 | 3/1980 | Lewis . | |
| 4,667,691 | 5/1987 | Sasa | 134/169 C |
| 4,785,940 | 11/1988 | Wilson | 206/632 |
| 4,903,718 | 2/1990 | Sullivan | 134/84 |
| 4,923,681 | 5/1990 | Cox et al. | 422/116 |
| 5,034,198 | 7/1991 | Kaiga et al. | 422/186.07 |
| 5,093,079 | 3/1992 | Bakaitis et al. | 422/28 |
| 5,288,467 | 2/1994 | Biermaier | 422/116 |
| 5,443,801 | 8/1995 | Langford | 422/294 |

FOREIGN PATENT DOCUMENTS

| | | |
|---|---|---|
| 0072257 | 2/1983 | European Pat. Off. . |
| 2 094 150 A | 9/1982 | Germany . |
| 2 199 496 A | 7/1988 | Germany . |
| WO 79 00590 | 8/1979 | WIPO . |

*Primary Examiner*—Krisanne Thornton

[57] ABSTRACT

An improved apparatus which can be used for cleaning and/or sterilizing tubular items. A container is partitioned into two chambers with the item to be cleaned and/or sterilized is positioned to extend through the partition such that one opening lies in one chamber and another opening lies in the other chamber. A flexible membrane is positioned to affect each chamber. By deforming the flexible membrane, inward and outward, a flow between the chambers is created. This flow must pass through the hollow item. Mechanical pressure from the flow cleanses the interior of the tubular item and if a sterilant is used as the medium, then the interior portion of the hollow item is also sterilized.

22 Claims, 7 Drawing Sheets

5,753,195

CLEANING AND STERILIZING MECHANISM

BACKGROUND OF THE INVENTION

This invention relates generally to mechanisms used to clean tubular items and more particularly to mechanisms used to sterilize as well.

The apparatus of this invention is particularly well suited for endoscope cleaning and sterilization. Other areas of application include: dental tools, surgical instruments, implants, etc.

Endoscopes are flexible tubes having a multiplicity of endings. Merely soaking endoscopes in a sterilant or detergent is unacceptable since numerous pockets exist within the tubing where the sterilant or detergent cannot reach effectively. This leaves areas of contamination within the endoscope. With the prevalence of highly contagious diseases such as hepatitis B and Acquired Immune Deficiency Syndrome, sterilization or disposal of all medical tools becomes mandatory.

Once used, endoscopes are usually discarded due to the complexity in getting the endoscope sterilized before any subsequent uses. Endoscopes themselves are extremely expensive so their disposal after one use is seen as wasteful since the structural integrity of the endoscope has not been jeopardized by its use, only its sterile nature.

It is clear from the foregoing that there is a significant need for a device which will assist in cleaning a device and improve the sterilizing affects.

SUMMARY OF THE INVENTION

In the present invention, an improved apparatus is created which can be used for cleaning and/or sterilizing of tubular items such as endoscopes.

Within this discussion, endoscopes will be used as an example of an item to be cleaned, but, the invention is not intended to be limited to this one item. Rather, the invention contemplates its use with any tubular item as well as a variety of other items such as circuit boards, medical instruments, dental instruments, and other items in which cleaning and/or sterilization is required.

In this invention, a container is partitioned into two chambers with the endoscope positioned to extend through the partition such that one opening of the endoscope lies in one chamber and another opening of the endoscope lies in the other chamber.

The partition between the chambers need not be an absolute partition and in the preferred embodiment, the partition fits loosely around the endoscope so that as the medium, (i.e. a liquid detergent, sterile water, a liquid sterilant, or a sterilant gas) surges from one chamber to the other, the medium washes over the exterior of the endoscope and is affected by the medium while the medium simultaneously sweeps through the interior of the endoscope.

In the creation of the surge, a flexible membrane is positioned to affect each chamber. By deforming the flexible membrane, inward and outward, a pressure or suction is created which results in a flow between the chambers to equalize the pressure between the chambers.

Deformation of the flexible membrane is accomplished in the preferred embodiment using air pressure which is exerted on an exterior portion of the membrane to deform it into the chamber; to accomplish the reverse flow, an external suction pulls the membrane from the chamber.

In the preferred embodiment, two flexible membranes or diaphragms are used. Each membrane addresses one of the chambers and the membranes are operated in a "reverse-gang" relationship. That is, as external pressure is being applied to one membrane, external suction is being applied to the other membrane. This reverse-gang relationship produces heightened medium flow within the container and increases the cleansing and/or sterilizing action.

This flow of medium must pass through the endoscope. Mechanical pressure from the medium flow assists in cleaning the endoscope. If a sterilant is used as the liquid medium, then the interior portion of the hollow item is also sterilized.

The preferred liquid sterilant is peracetic acid and the preferred gas sterilant is ethylene-oxide (ETO). Those of ordinary skill in the art readily recognize various other sterilants which can be used in this context.

By reversing the flow between the chambers, a "scrubbing" action is created which dislodges and removes debris and other contaminants from the interior and exterior of the endoscope.

In some embodiments of the invention, a soak or solvent is used to help break down or loosen the debris. This step is particularly useful for the removal of protein or fat particles.

In the preferred embodiment, the endoscope is first cleaned using a detergent. Afterwards, a sterilant is applied using a gentle flow between the chambers. In some embodiments of the invention, the pumping action is stopped to permit the sterilant to rest against the endoscope's interior and exterior so that a maximum sterilizing affect is obtained.

As a final step in the preferred embodiment, the sterilant is removed and sterile water is washed over and through the endoscope in preparation for subsequent use with a patient. Some embodiments of the invention also add a lubricant rinse and soak to extend the life of the endoscope.

The invention, together with various embodiments thereof will be more fully explained by the accompanying drawings and the following descriptions.

DRAWINGS IN BRIEF

DRAWINGS IN DETAIL

Figure 1:
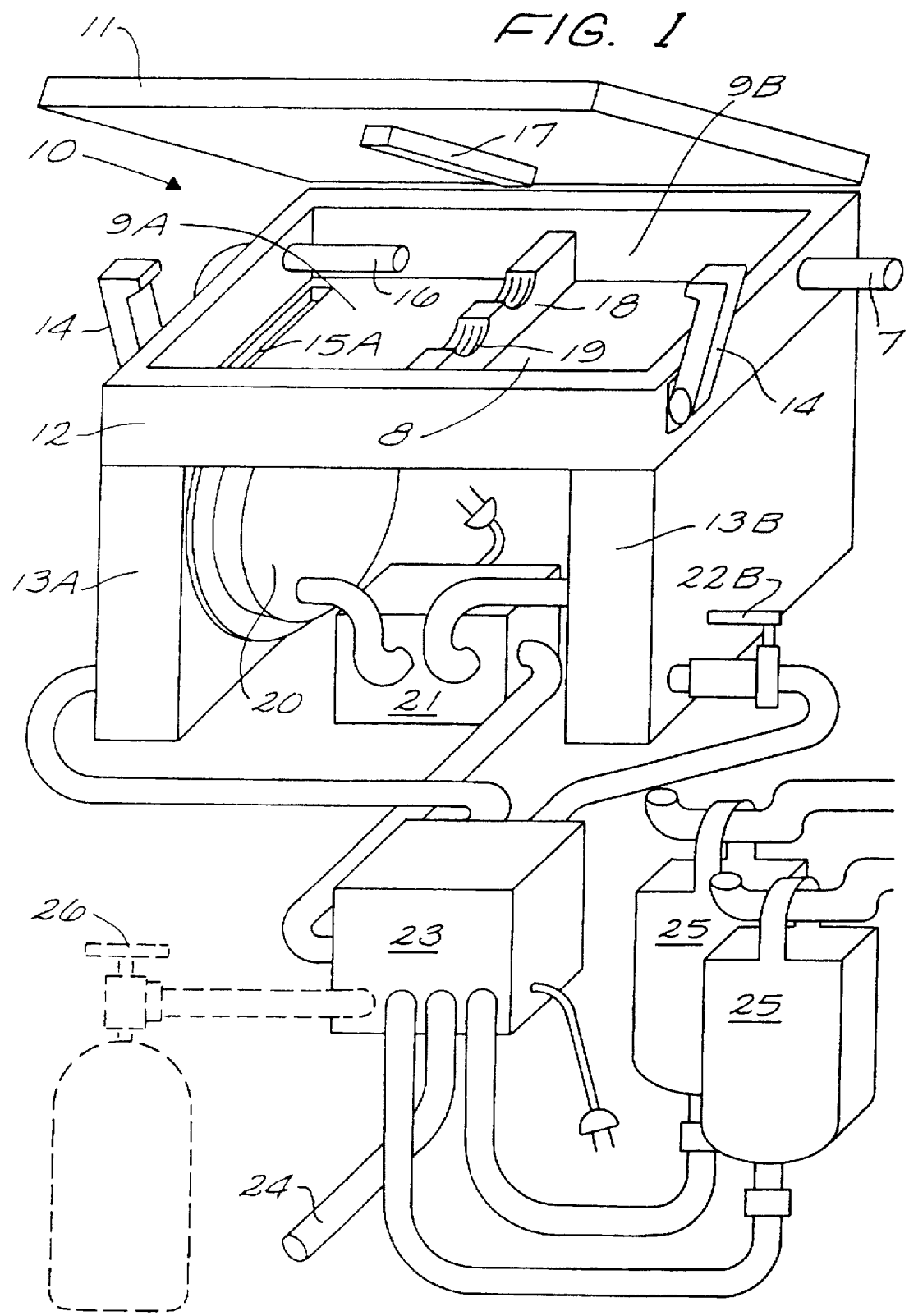
FIG. 1 is a layout view of the preferred embodiment of the invention.

FIG. 1 is a layout view of the preferred embodiment of the invention.

Cleaner 10 has five major components: lid 11; base unit 12 with legs 13A and 13B; membrane pump 21; controller and valves 23 and reservoirs 25 (or alternatively gas tanks 26).

Lid 11 is hinged to base unit 12 and is secured in a closed position by latches 14. Lid 11 is sealed around its periphery with base unit 12 to form an air tight container.

Seal 17 is designed to mate with seal 18 to divide container 8 into chambers 9A and 9B. The endoscope, not shown, is positioned to pass through recesses 19 in seal 18 such that one end of the endoscope lies in chamber 9A while the other end of the endoscope lies in chamber 9B. When lid 11 is closed and sealed, seal 17 completes the seal around the endoscope.

In this embodiment, each leg, 13A and 13B, are hollow and communicate with container 8 via an opening such as opening 15A.

Each leg 13A and 13B is also provided with a port such as port 22B through which a medium (a liquid or gas) is communicated. By supplying a medium to the port, and since the hollow leg communicates with container 8, the container is filled with whatever medium is desired.

Each leg further includes a flexible membrane 20 which communicates with the hollow portion of the leg.

Membrane pump 21 is used to selectively deform flexible membrane 20 and in so doing create a pumping action through container 8.

Membrane pump 21 is controlled by controller and valves 23 which acts as the central "brains" in controlling the operation of the apparatus. When the endoscope has been properly placed within container 8 and lid 11 has been closed, controller 23 draws a selected medium, a liquid in this illustration, from reservoirs 25 and communicates this liquid to port 22B. In an alternative embodiment, a gas from container 26 is used as the medium.

Once container 8 has been properly filled, controller 23 initiates a pumping action via pump 21 and the flexible membranes 20. The pumping action from pump 21 oscillates between a pressure and a suction so that each flexible membrane moves inward and outward to cause the medium to flow between chamber 9A and 9B.

The medium flow between the chambers 9A and 9B naturally flows through the endoscope and as such forces the medium throughout the endoscope. In a cleaning operation, the mechanical force exerted by the medium removes debris from the inside of the endoscope.

In the preferred order of cleaning and sterilizing, the steps taken by the operator are:

Step 1: Placement of endoscope into container 8, closure of lid 11, and securement of lid 11 via clamps 14; and, Step 2: Initiate process by activating controller 23.

The system then proceeds through its sequence of steps:

Step 1: Container 8 is filled with an enzyme/solvent to loosen protein and fat from the walls of the endoscope;

Step 2: Fill container 8 with a detergent from one of the reservoirs 25;

Step 3: Agitate by oscillating a pumping action between chambers 9A and 9B using pump 21 and flexible membranes 20;

Step 4: Drain container 8 and discharge into drain 24;

Step 5: Fill container 8 with a sterilizing agent such as ozone, or others known to those of ordinary skill in the art, from one of the reservoirs 25;

Step 6: Gently oscillate the sterilizing agent through the endoscope using pump 21 and membranes 20 (a lubricant may be added at this point);

Step 7: Permit the sterilizing agent to stand within the endoscope;

Step 8: Gently oscillate the sterilizing agent through the endoscope using pump 21 and membranes 20;

Step 9: Drain container 8 and discharge into drain 24 while heating container via heating element 16 (an alternative technique is to dry using filtered air).

As a quality control mechanism, sampler 7 is solenoid driven and draws a sample of the liquid or gas medium within container 8. This sample is then subjected to testing using chemical and biological indicators which reveal if the sterilizing process has been successful.

Heater element 16 is used to vaporize any liquids so that they too can be drawn from container 8 to leave a clean, sterile, and dry, endoscope within container 8.

In an alternative embodiment, filtered ambient heated air is pumped through container 8 to dry the items therein.

Figure 2:
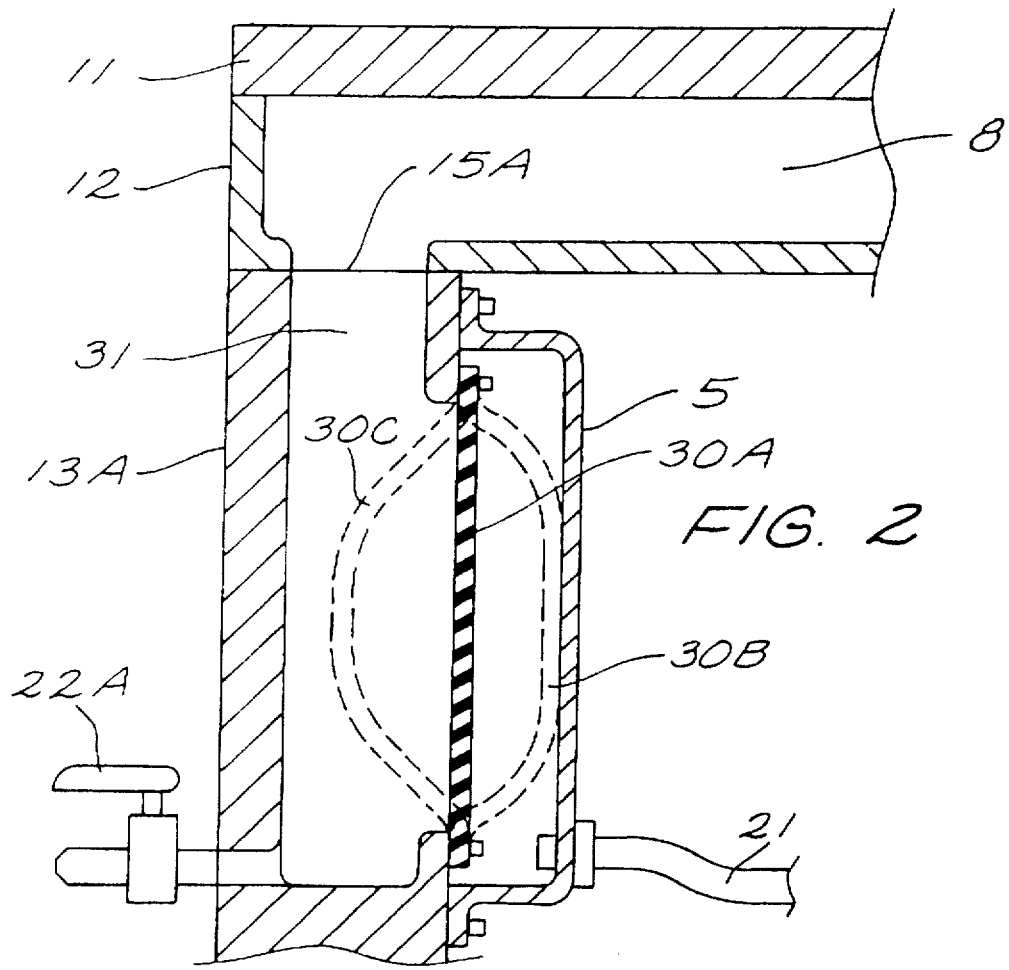
FIG. 2 is a close-up view of one of the membranes illustrated first in FIG. 1.

FIG. 2 is a close-up view of one of the membranes illustrated first in FIG. 1.

As before, base unit 12 includes a container 8 which communicates with leg 13A via opening 15A. Port 22A permits the introduction and withdrawal of medium from container 8.

Hollow portion 31 is within leg 13A and is in communication with flexible membrane 30A. Positioned over flexible membrane 30A is a rigid cover 5. A pipe/tube communicates an interior formed by the rigid cover 5 with pump 21. Pump 21, because of this arrangement, is able to either pressurize or de-pressurize the interior portion of rigid cover 5. In so doing, flexible membrane 30A deforms inward, 30C, under pressure; and draws outward, 30B, in a suction mode.

This movement of flexible membrane 30A between positions of 30B and 30C, provides a pumping action which pushes and pulls medium through container 8.

Figure 3:
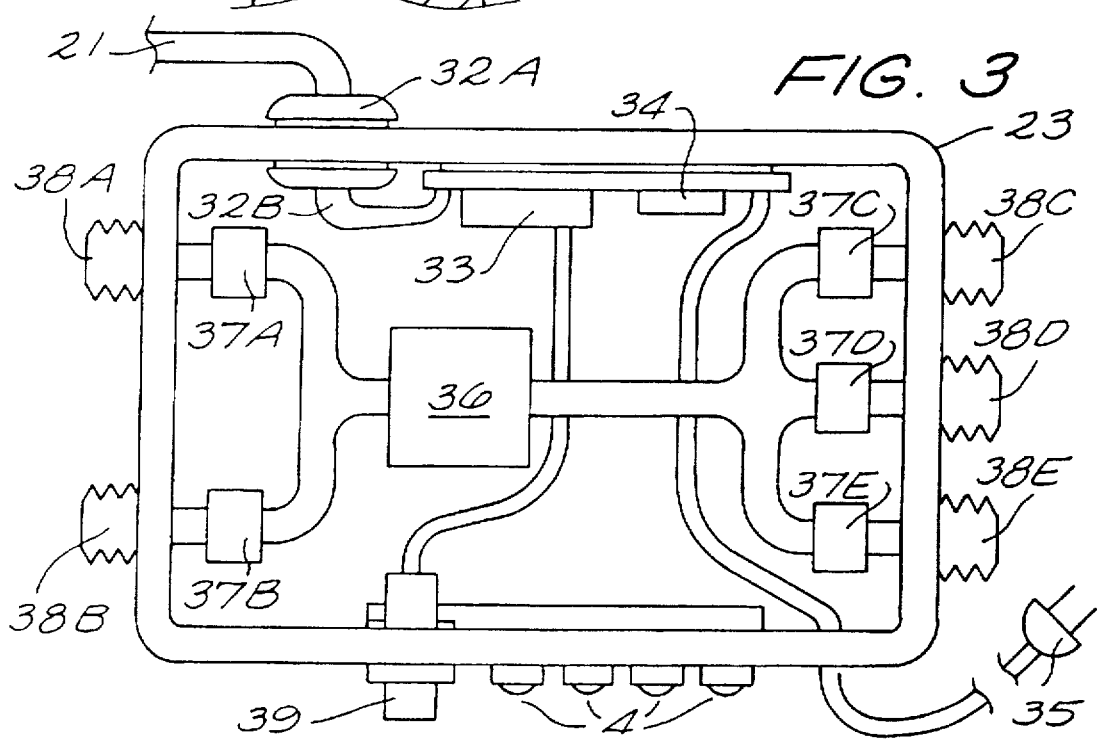
FIG. 3 is a layout of the preferred controller/valve system.

FIG. 3 is a layout of the preferred controller/ valve system.

Controller with valves 23 communicates the medium using fittings 38A, 38B, 38C, 38D, and 38E. Each fitting is opened or closed using solenoids 37A, 37B, 37C, 37D, and 38E respectively. All of these communicate with pump 36 to form the valving system.

Connected to pump 36 and each solenoid 37A, 37B, 37C, 37D, and 37E, is controller chip 33 which is used to coordinate all operation. Power to controller chip 33 is provided by standard electrical outlets 35 which passes through an appropriate transformer to provide proper voltage and current for the demands of the electronic system. Those of ordinary skill in the art readily recognize which transformers are to be used in this context.

Timing chip 34 provides a timing base from which controller 33 operates.

Controller 33 further communicates with membrane pump 21 via connector 32A and 32B.

Initiation of the operation is communicated by operator activation of button 39. Thereafter, controller 33 communicates a status report using lights 4 which are selectively activated during operation of the apparatus.

Figure 4:
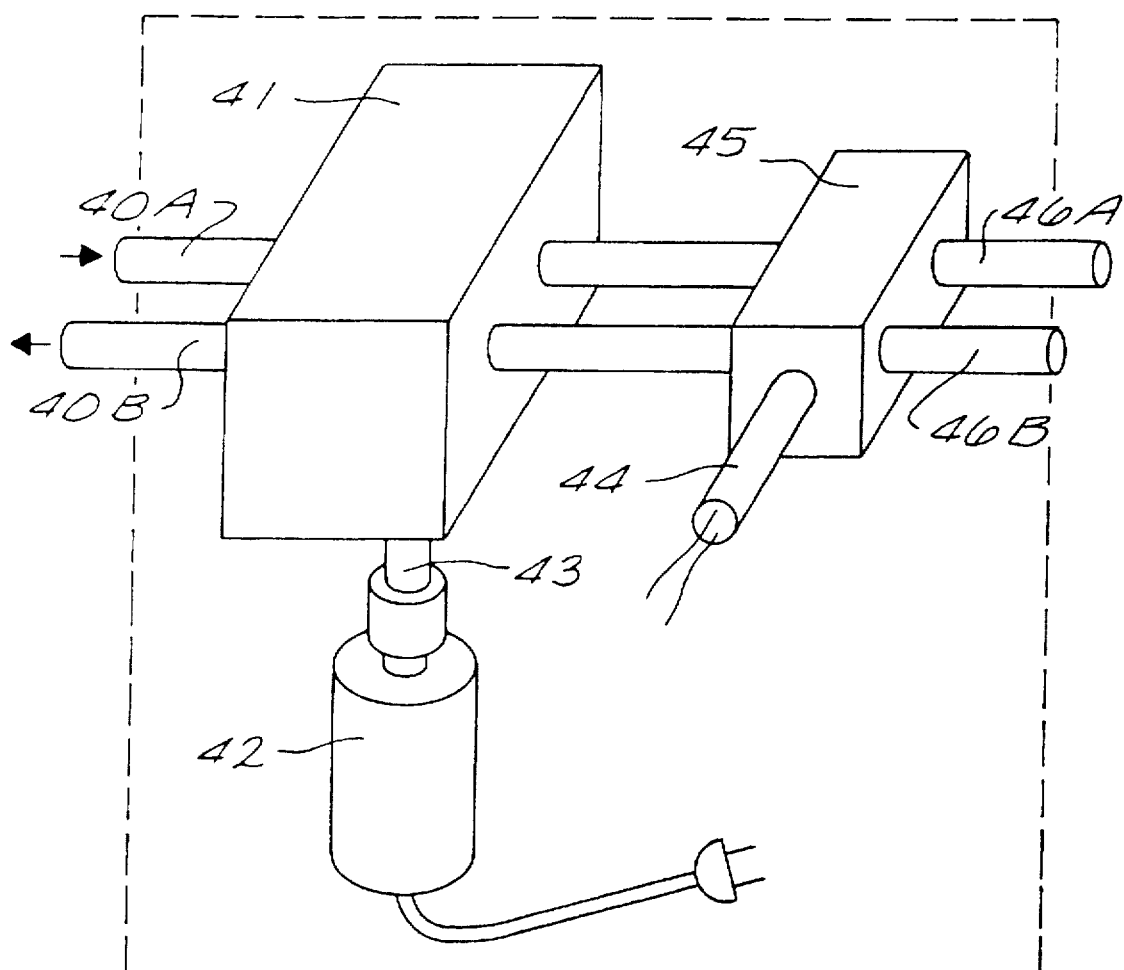
FIG. 4 is a schematic of the pump illustrated in the embodiment of FIG. 1.

FIG. 4 is a schematic of the pump illustrated in the embodiment of FIG. 1.

Membrane pump 21 is composed of a piston block 41 which includes two pistons. These pistons are driven by electric motor 42 and drive shaft 43. One piston draws in air 40A while the other piston exhausts air 43B. The pressure and suction from piston block 41 is communicated to valve block 45.

Valve block 45 is a reciprocating valve which is operated by solenoid 44. As a reciprocating valve, valve block 45 selectively directs the pressure to either port 46A or port 46B; simultaneously, the suction provided from piston block 41 is directed to the other port. As example, when pressure is supplied to port 46A, suction is provided to port 46B, and vice versa.

In this manner, for a two flexible membrane system, while one membrane is being pressured into the hollow of one leg, the other membrane is being drawn from the hollow of its leg. This dual action creates a more dramatic pumping action and creates a greatly enhanced cleaning potential.

Figure 5A:
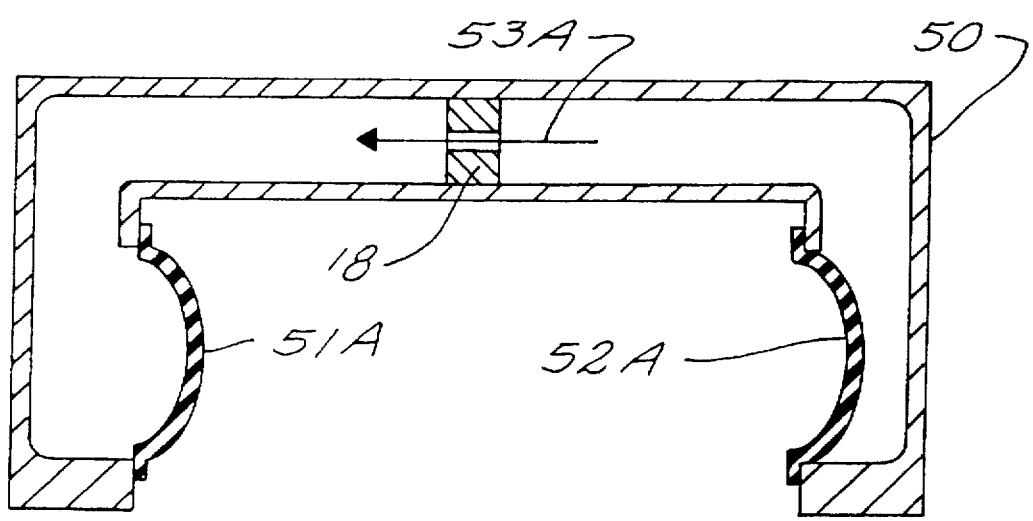
FIGS. 5A and 5B are side views illustrating two membranes working in a gang relationship to create the desired surge.
Figure 5B:
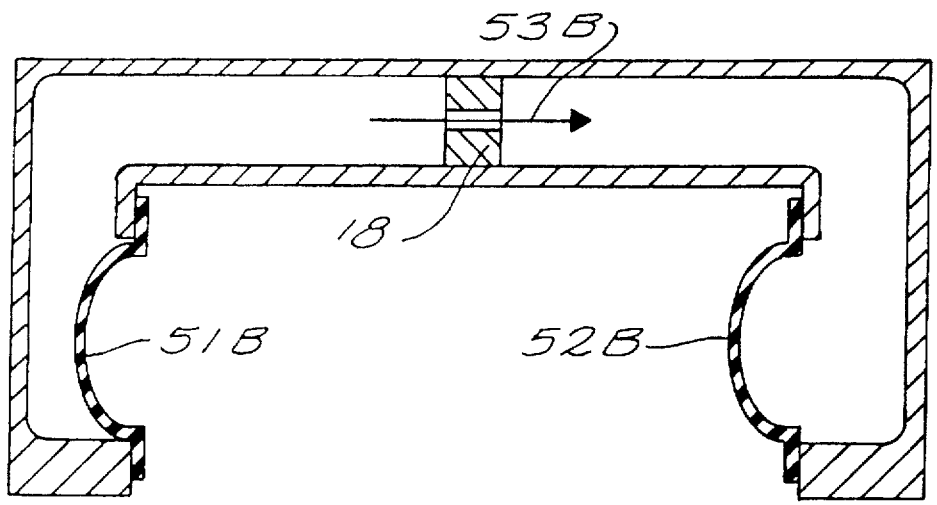

FIGS. 5A and 5B are side views illustrating two membranes working in a gang relationship to create the desired surge.

As shown in simplified form in FIG. 5A, for the cleaner/sterilizer 50, by drawing flexible membrane 51A from the hollow in the leg while forcing flexible membrane 52A into the hollow, the medium flows as indicated by arrow 53A through partition 18.

In opposite fashion, by pressing flexible membrane 51B into the hollow and drawing flexible membrane 52B from the hollow, the flow of medium is reversed as shown by arrow 53B.

Through the selective oscillation between the two states shown in FIGS. 5A and 5B, the flow of medium through the endoscope, not shown, is continuously reversed creating a scrubbing affect in the endoscope.

Figure 6:
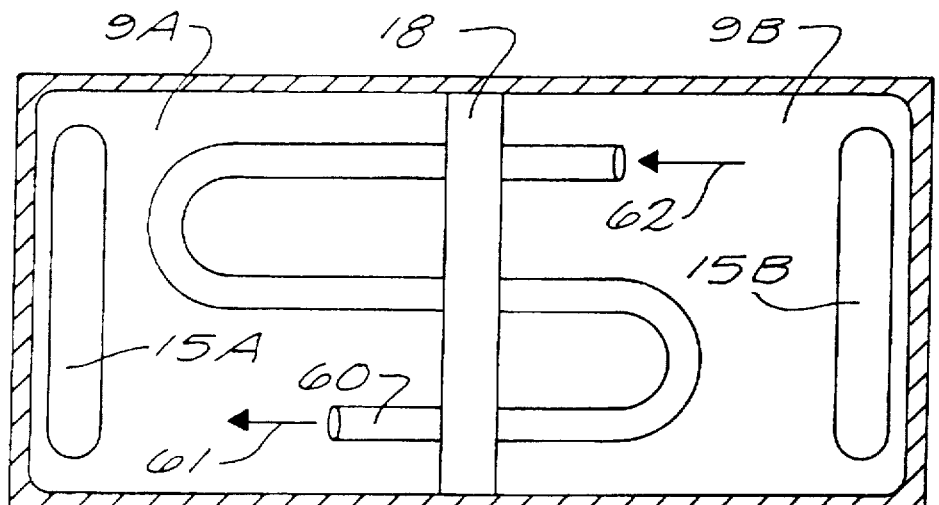
FIG. 6 is a top view illustrating the flow from one chamber to another through the endoscope.

FIG. 6 is a top view illustrating the flow from one chamber to another through the endoscope.

Endoscope 60 is position through seal 18 as described above so that one end of endoscope lies in chamber 9A while the other end lies in chamber 9B. By the pumping action described above, medium is either drawn or expelled through openings 15A and 15B into chambers 9A and 9B respectively. This pumping action forces the medium to flow into one end of endoscope 60, as illustrated by arrow 62, and to exit out the other end, as illustrated by arrow 61.

The flow of the medium through endoscope 60 flushes debris from the interior of the endoscope and significantly enhances the operation over the prior art.

Figure 7:
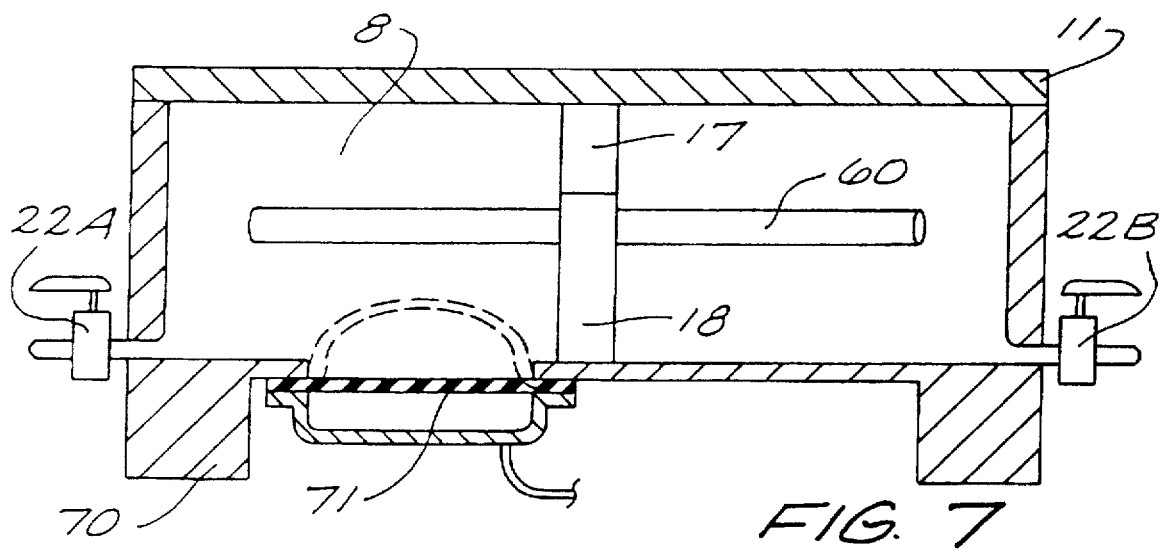
FIG. 7 is an alternative embodiment of the invention in which a single membrane is used.

FIG. 7 is an alternative embodiment of the invention in which a single membrane is used.

In this embodiment of cleaner/sterilizer 70, a single membrane 71 is used to create the pumping action with container 8. As before, endoscope 60 is positioned to extend through the partition formed by seal 18 and seal 17. As membrane 71 is pressed into container 8, a surge of the medium flows through endoscope to assist in cleansing of the interior of the endoscope.

Ports 22A and 22B provide for drainage and filling openings so that the selected medium can be installed and drained from container 8.

Note that in this embodiment, membrane 71 communicates directly with container 8 and as such, the legs of cleaner 70 can be shortened permitting this embodiment to be used in many locations where space is a concern.

Figure 8:
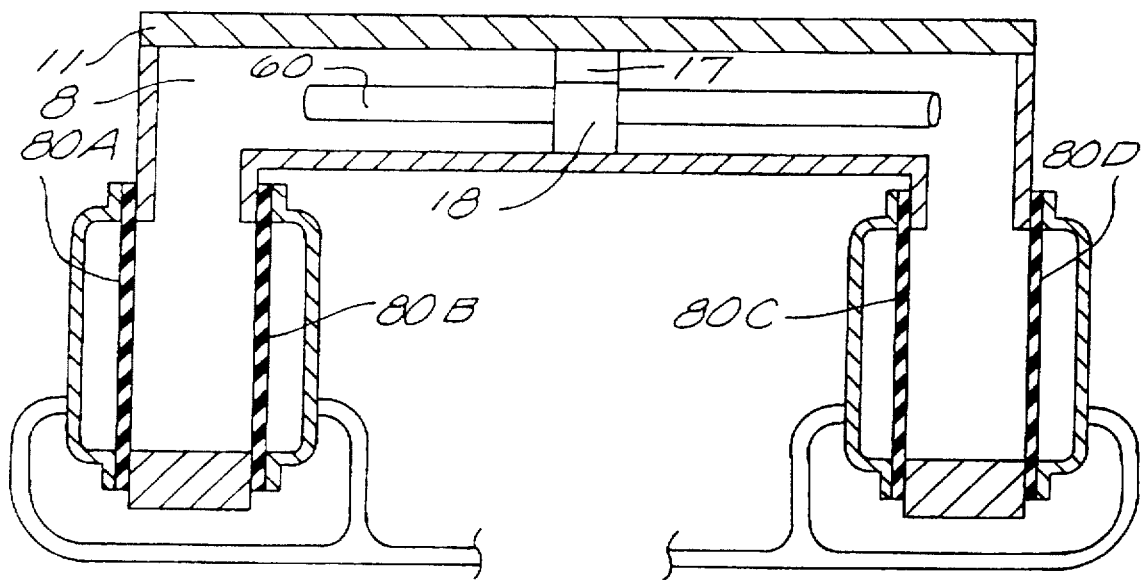
FIG. 8 is an alternative embodiment of the invention in which four membranes are utilized to create more surge effect.

FIG. 8 is an alternative embodiment of the invention in which four membranes are utilized to create more surge effect.

Again, endoscope 60 is positioned within container 8 through seal 17 and seal 18. In this embodiment, to provide for an even greater surge of the medium through endoscope 60, four membranes 80A, 80B, 80C, and 80D, are used in a gang relationship with the membranes combined in pairs to work simultaneously to provide either pressure or suction pumping. As example, when membrane 80A is pressurized, so is membrane 80B.

Those of ordinary skill in the art readily recognize that any number of membranes may be used in this context. By varying the number of membranes used, the designer is able to obtain the desired pumping action, and as an extension, the surge.

Figure 9:
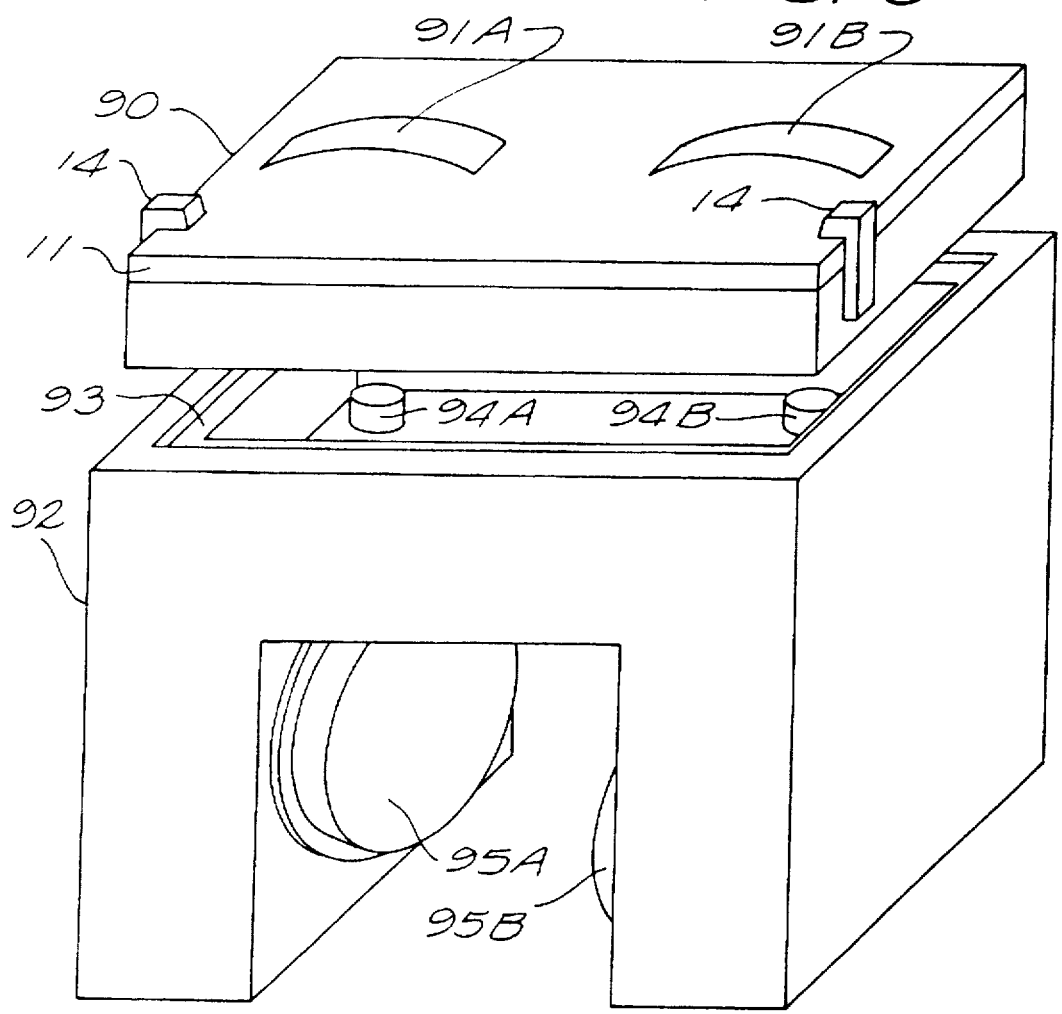
FIG. 9 is a perspective view of an embodiment in which the container is removable from the membrane system.

FIG. 9 is a perspective view of an embodiment in which the container is removable from the membrane system.

Cleaner 92 provides a seat 93 into which container 90 is nested. During the nesting process, valves 94A and 94B mate with their reciprocal parts, not visible in this view, of container 90. Valves 94A and 94B, and their reciprocal counterparts, seal upon disengagement so that the contents of container 90 maintain their clean and/or sterile integrity when container 90 has been removed. This permits the endoscope to be cleaned and/or sterilized and then stored without fear of contamination. When the surgeon is ready to utilize the endoscope, removal of clamps 14 and the lifting of lid 11 makes the sterile endoscope available for use.

As discussed before, flexible membranes 95A and 95B are located on base member 92 and provide the pumping action discussed. This pumping action is communicated to container 90 via valves 94A and 94B. The operation of this cleaner is similar to that already discussed.

Removal of container 90 is facilitated using handles 91A and 91B. Once removed, container 90 may be stored for later use or may be opened for immediate use of the endoscope.

Figure 10:
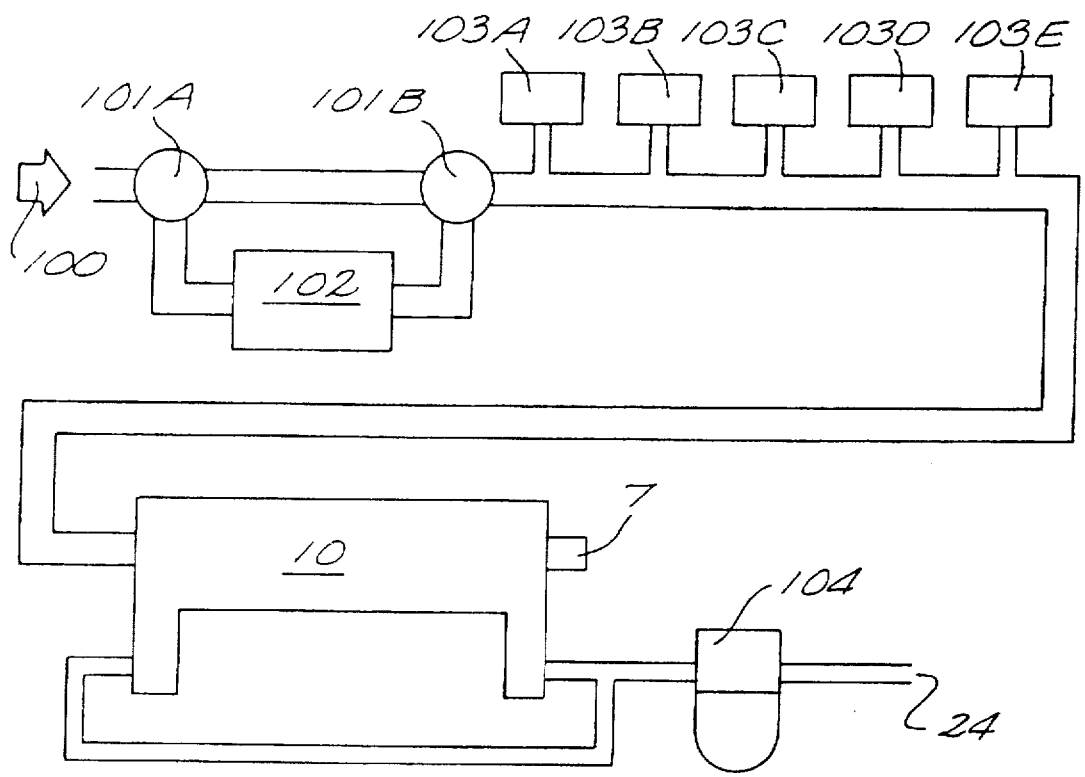
FIG. 10 is a block diagram of the layout of an embodiment of the invention.

FIG. 10 is a block diagram of the layout of an embodiment of the invention.

Water source 100 is directed, by way of valves 10A and 101B, to either continue on its course or to pass through flash heater 102. Flash heater 102 is chosen to heat the water to a desired temperature which is of optimal assist for a medium contained in one of the reservoirs.

Reservoirs 103A, 103B, 103C, 103D, and 103E, in this embodiment, contain an enzyme soak (used to loosen fats and proteins from the skin of the endoscope), a detergent (used to wash debris from the endoscope), an acid sanitizer (used to adjust the PH within the container), a sterilant (used to sterilize the endoscope), and a lubricant (used to lubricate the endoscope for use in the surgical field), respectively. The controller, not shown in this illustration, controls the valves 101A and 101B as well as the injection of medium from the various reservoirs 103A, 103B, 103C, 103D, and 103E.

As a safety feature, each reservoir is identified by an electronic chip which communicates with the controller. This chip absolutely identifies the reservoir's contents so that an improperly connected reservoir cannot discharge its contents at the wrong time.

The stream is then directed to the cleaner/sterilizer 10 where the proper operation is conducted as outlined above. At the option of the operator, sampler 7 draws a medium sample from the container. This sample is used to confirm that the endoscope has been properly cleaned and sterilized.

At selected points with the operation, the medium is drained from cleaner/sterilizer 10 and the material passes through indicator 104 where the material is tested by a chemical and biological indicator to assure that unacceptable contaminants do not pass to drain 24.

In one embodiment, a second flash heater is used after indicator 104. This flash heater is designed to heat the discharge to such a temperature that all biological contaminates are destroyed prior to discharge into the drain. Yet another embodiment positions a flash heat before indicator 104 to accomplish the same task.

Figure 11A:
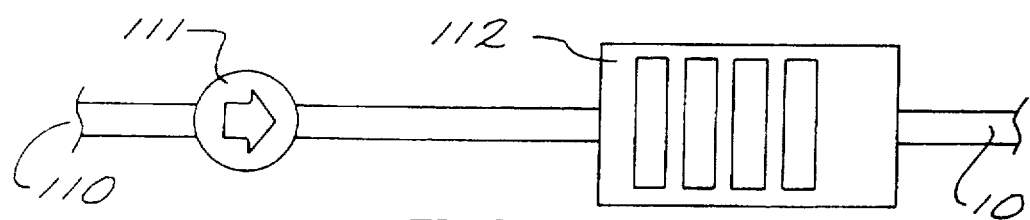
FIG. 11A is a block diagram of the drying mechanism of the preferred embodiment which uses ambient air.

FIG. 11A is a block diagram of the drying mechanism of the preferred embodiment which uses ambient air.

In some situations, the use of ambient air 110 is made to assist in the drying of the endoscope within the cleaner/ sterilizer. For ambient air to be properly used, pump 111 pushes the air through filters 112 prior the air being passed along to cleaner 10.

Filters 112 are chosen to remove particles (including biological agents) from the air so that the endoscope within the cleaner 10 is not re-contaminated. Those of ordinary skill in the art readily recognize various filters which can be used in this context.

Figure 11B:
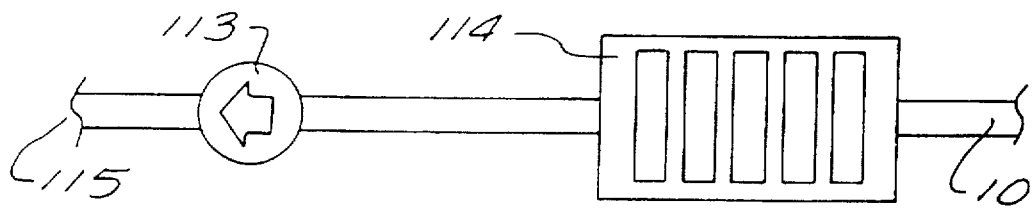
FIG. 11B is a block diagram of the purging mechanism used to purge gas from the cleaner/sterilizer.

FIG. 11B is a block diagram of the purging mechanism used to purge gas from the cleaner/sterilizer.

When a sterilizing gas is used within the container, it is adviseable to purge the container of the gas. This is accomplished safely through the use of filter 114 through which blower 113 draws the gas from cleaner 10. If peracetic acid is used as the sterilizing gas, filters 114 are preferably moistened sponges. In other embodiments, activated charcoal is used to cleanse the gas before it is discharged as exhaust 115.

Those of ordinary skill in the art readily recognize various other filters which can be used in this context.

Figure 12A:
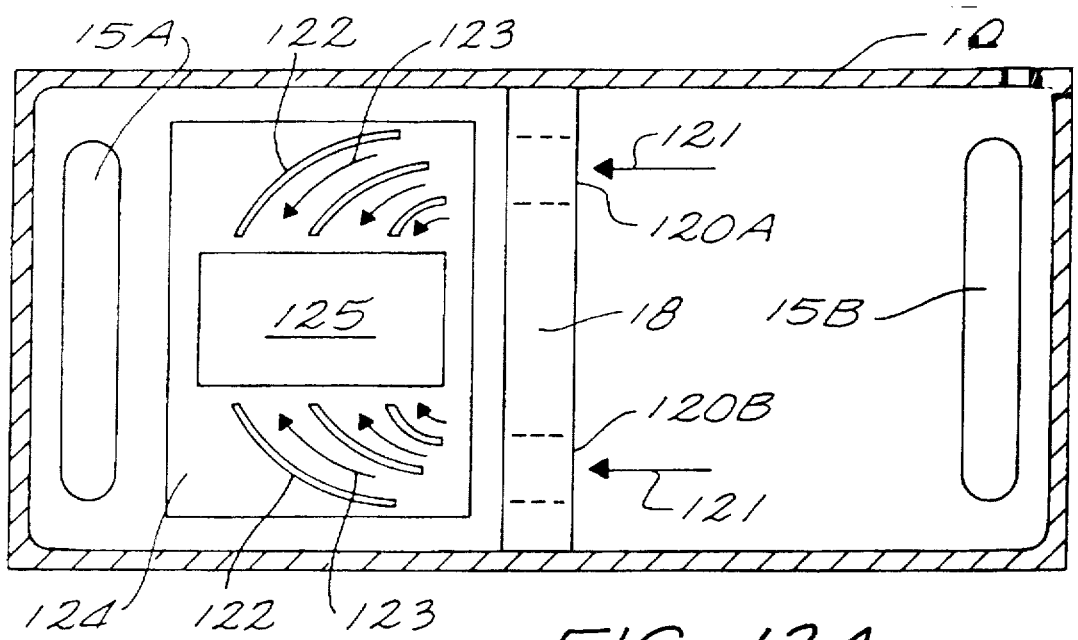
FIGS. 12A and 12B are top and side views of an embodiment of the invention in which flat items are cleaned.
Figure 12B:
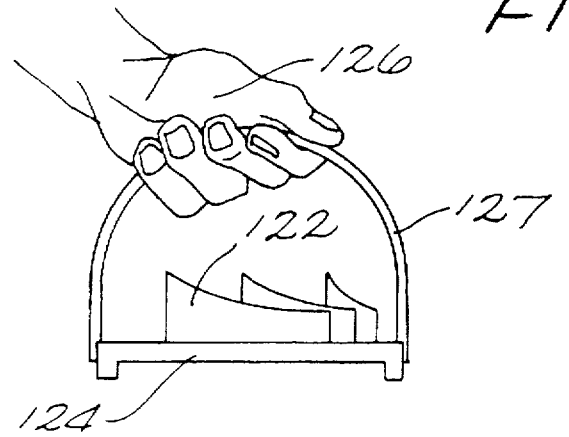
Figure 12B:
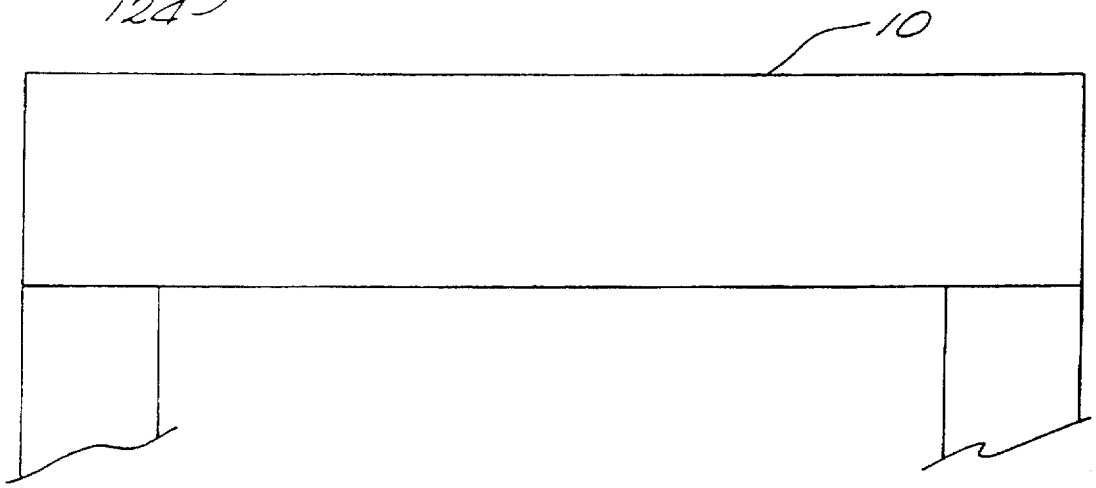

FIGS. 12A and 12B are top and side views of an embodiment of the invention in which flat items are cleaned.

Operator 126 uses handle 127 and caddie 124 to place item 125 (a printed circuit board in this illustration) into cleaner 10. Cleaner 10 operates as described above with drains 15A and 15B communicating with the membranes (not shown in this illustration).

In this embodiment, partition 18 is slightly wider and contains notch type passages 120A and 12B through which the surge of medium flows, as illustrated by arrows 121. Vanes 122 redirect the flow as indicated by arrows 123 to pass the medium over item 125.

Through selective design of vanes 122, caddie 124 is designed to address the cleaning needs of a variety of different items so that optimal cleaning is obtained.

It is clear from the foregoing that the present invention creates a highly improved cleaner for hollow items and also provides for the ability to sterilize hollow items in a way heretofore unattainable.

What is claimed is:

1. A cleaning mechanism comprising:
   a) a container for enclosing a tubular item to be cleaned, said container having a barrier therein dividing said container into a first chamber and a second chamber, said tubular item positioned to extend from said first chamber to said second chamber; and,
   b) oscillating means having,
      1) a first flexible membrane in communication with said first chamber,
      2) a second flexible membrane in communication with said second chamber, and,
      3) pressure means for providing external pressure to one of said flexible membranes and simultaneously providing suction to another one of said flexible membranes.

2. The cleaning mechanism according to claim 1 further including clock means for controlling a period of time between oscillating of said pressure means.

3. The cleaning mechanism according to claim 2 further including;
   a) means for introducing gas and liquids into said container; and,
   b) means for exhausting gas and liquids from said container.

4. The cleaning mechanism according to claim 3 further including:
   a) at least two reservoirs containing selected liquids; and,
   b) control means in communication with said at least two reservoirs, said means for introducing, and said means for exhausting, said control means for,
      1) selectively introducing liquids from a selected one of said at least two reservoirs into said container via said means for introducing, and,
      2) exhausting liquids from said container via said means for exhausting.

5. The cleaning mechanism according to claim 1 further including:
   a) a first hollow leg member supporting one side of said container, a hollow portion of said first hollow leg member in communication with said first flexible membrane and said first chamber; and,
   b) a second hollow leg member supporting a second side of said container, a hollow portion of said second hollow leg member in communication with said second flexible membrane and said second chamber.

6. The cleaning mechanism according to claim 1 wherein said first flexible membrane and said second flexible membrane are deformed by air pressure.

7. The cleaning mechanism according to claim 1 further including heating means for selectively heating an interior of said container.

8. The cleaning mechanism according to claim 3 wherein said means for exhausting communicates with a drain.

9. An apparatus for cleaning an item, said apparatus comprising:
   a) a first chamber;
   b) a second chamber, a portion of said item positioned in said first chamber;
   c) a first hollow leg member supporting one side of said container, a hollow portion of said first hollow leg member in communication with at least one flexible membrane and said first chamber;
   d) a second hollow leg member supporting a second side of said container; and,
   e) oscillating pressure means for alternatively applying external pressure and external suction against said at least one flexible membrane.

10. The apparatus according to claim 9 further including;
    a) means for introducing a medium into said container; and,
    b) means for exhausting a medium from said container.

11. The apparatus according to claim 10 further including:
    a) at least two reservoirs containing mediums; and,
    b) control means in communication with said at least two reservoirs, said means for introducing, and said means for exhausting, said control means for,
       1 selectively introducing medium from a selected one of said at least two reservoirs into one of said chambers via said means for introducing, and,
       2) selectively exhausting medium from one of said chambers via said means for exhausting.

12. The apparatus according to claim 9 further including means for drawing a sample of medium from said first chamber without breaking a seal surrounding said first chamber.

13. The apparatus according to claim 9 further including:
    a) pump means for pumping ambient air;
    b) filter means for restricting particles in air from said pump of a chosen size and larger from passing therethrough; and,
    c) means for introducing air from said filter means into said first chamber.

14. The apparatus according to claim 9 further including:
a) a filter; and,
b) means for drawing gas from said first chamber and said second chamber through said filter and then exhausting said gas into the atmosphere.

15. A cleaning and sterilizing mechanism comprising:
a) a container for enclosing a tubular item, said container having a barrier therein dividing said container into a first chamber and a second chamber, said tubular item positioned to extend from said first chamber to said second chamber, said container positioned substantially level and further having,
   1) a first hollow leg supporting a first edge of said container, a hollow portion of said first hollow leg in communication with said first chamber, and,
   2) a second hollow leg supporting a second edge of said container, a hollow portion of said second hollow leg in communication with said second chamber;
b) a membrane system having,
   1) a first flexible membrane in communication with the hollow portion of said first hollow leg, and,
   2) a second flexible membrane in communication with the hollow portion of said second hollow leg; and,
c) pressure means for selectively applying pressure against one of said flexible membranes of said membrane system.

16. The mechanism according to claim 15 wherein said pressure means includes means for providing external pressure to one of said flexible membranes and simultaneously providing external suction to another one of said flexible membranes.

17. The mechanism according to claim 16 further including clock means for controlling a period of time between oscillating said pressure means.

18. The mechanism according to claim 17 further including;
a) means for introducing gas and liquids into said container via said first hollow leg; and,
b) means for exhausting gas and liquids from said container via said second hollow leg.

19. The mechanism according to claim 15 further including:
a) at least two reservoirs; and,
b) control means in communication with said at least two reservoirs, said means for introducing, and said means for exhausting, said control means for,
   1) selectively introducing liquids from one of said at least two reservoirs into said container via said means for introducing, and,
   2) exhausting liquids from said container via said means for exhausting.

20. The mechanism according to claim 15 wherein said pressure means communicates force via air pressure.

21. The mechanism according to claim 15 further including heating means for selectively heating an interior of said container.

22. The mechanism according to claim 15 wherein said means for exhausting communicates with a drain.

* * * * *